United States Patent [19]

Salerno et al.

[11] Patent Number: 4,924,855

[45] Date of Patent: May 15, 1990

[54] LARYNGOSCOPE BLADE

[76] Inventors: Albert Salerno, 10830 Carla Pl., Cerritos, Calif. 90701; Gabor Racz, 4504 17th St., Lubbock, Tex. 79416

[21] Appl. No.: 223,388

[22] Filed: Jul. 25, 1988

[51] Int. Cl.$^5$ .............................................. A61B 1/06
[52] U.S. Cl. ..................................................... 128/11
[58] Field of Search ............... 128/11, 16, 10; D24/18

[56] References Cited

U.S. PATENT DOCUMENTS

| | | | |
|---|---|---|---|
| 2,289,226 | 7/1942 | Von Foregger | 128/16 |
| 2,359,971 | 7/1944 | Macintosh | 128/10 |
| 3,426,749 | 2/1969 | Jephcott | 128/11 |
| 3,826,248 | 7/1974 | Gobels | 128/11 |
| 3,856,001 | 12/1974 | Phillips | 128/11 |
| 3,986,854 | 10/1976 | Scrivo et al. | 128/11 |
| 4,112,933 | 9/1978 | Moses | 128/11 |
| 4,114,609 | 9/1977 | Moses | 128/11 |
| 4,273,112 | 6/1981 | Heine et al. | 128/11 |
| 4,306,597 | 12/1981 | Lowell | 128/11 |
| 4,314,551 | 2/1982 | Kadell | 128/11 |
| 4,406,280 | 9/1983 | Upsher | 128/11 |
| 4,432,350 | 2/1984 | Breslaw et al. | 138/10 |
| 4,556,052 | 12/1985 | Muller | 128/16 |
| 4,583,527 | 4/1986 | Musicant et al. | 128/11 |
| 4,592,343 | 6/1986 | Upsher | 128/11 |

FOREIGN PATENT DOCUMENTS 2381528  10/1978  France .................... 128/11

OTHER PUBLICATIONS

Periodical entitled *Anaesthesia*, vol. 39, No. 12 published Dec., 1984, article entitled "Improved Vision Modification of the Macintosh Laryngoscope", by G. B. Racz, pp. 1245–1250.
Advertising Brochures (2) Anesthesia Medical Specialties discloses Two Types of Laryngoscope Blades.

*Primary Examiner*—Edward M. Coven
*Assistant Examiner*—M. Graham
*Attorney, Agent, or Firm*—Trask, Britt & Rossa

[57] ABSTRACT

A laryngoscope blade having a base member and a blade portion. The blade portion is curved throughout its entire length. The blade portion defines a recessed channel in the top surface thereof, positioned approximately midway between the ends of the blade portion.

17 Claims, 2 Drawing Sheets

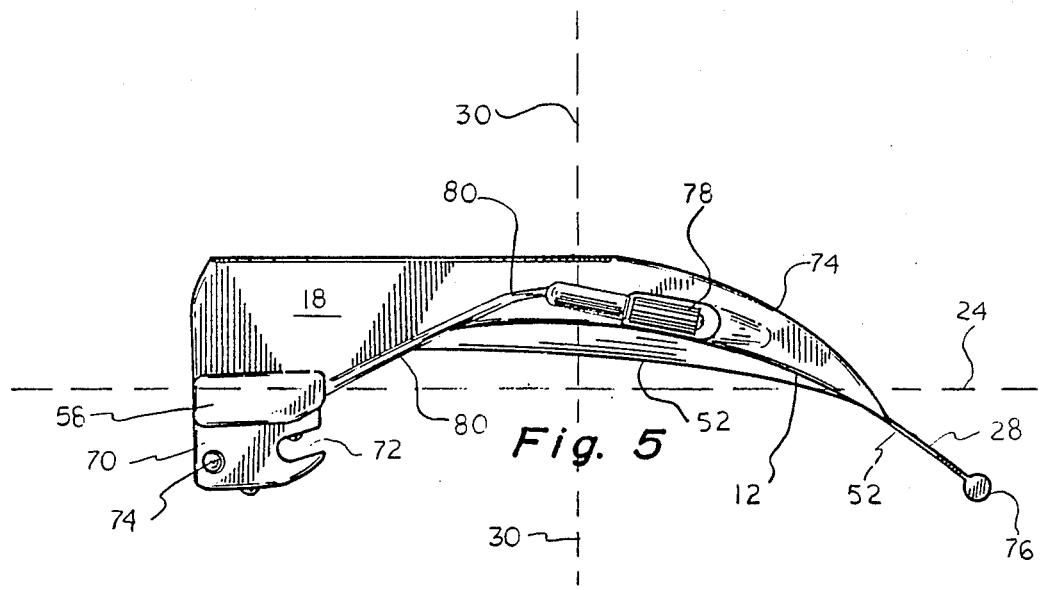
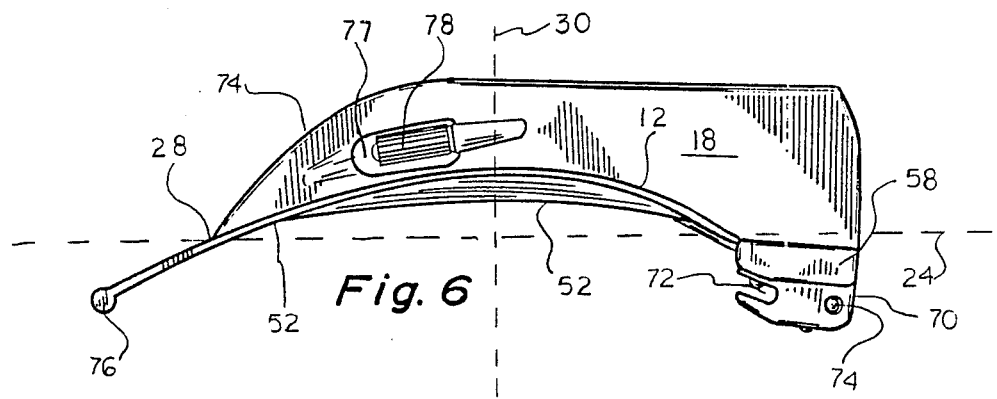
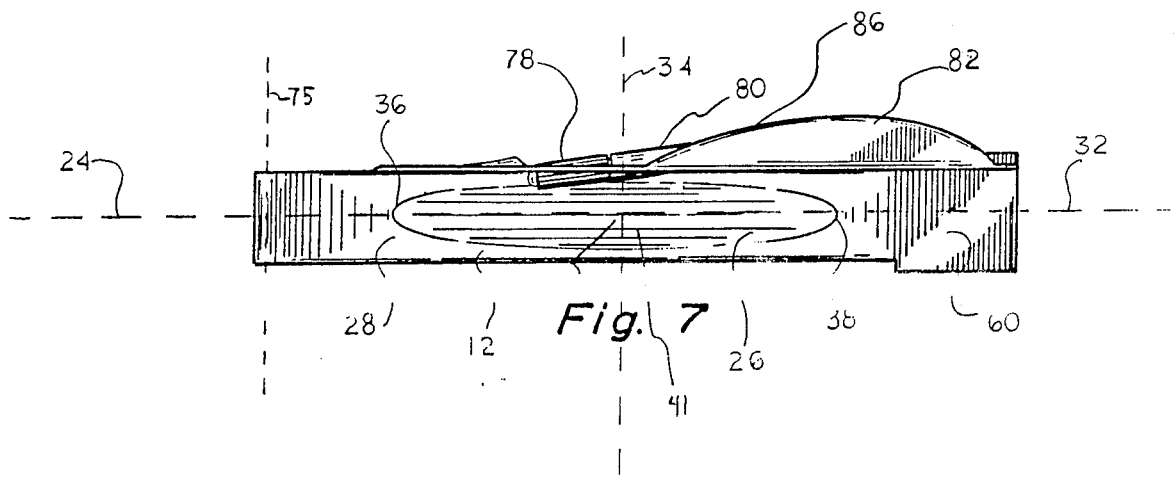

LARYNGOSCOPE BLADE

This application is related to application Ser. No. 752,541 filed July 8, 1985, entitled Laryngoscope Blade and presently issued as U.S. Pat. No. D. 293,363.

FIELD

This invention relates to laryngoscope blades. More particularly, this invention is directed to an improvement of the Macintosh-type laryngoscope blade.

STATEMENT OF THE ART

Laryngoscopes of various constructions and configurations have previously been proposed.

U.S. Pat. No. 4,556,052 issued on Dec. 3, 1985 to Rolf Muller and entitled MEDICAL INSTRUMENT WITH INTERNAL LIGHT SOURCE FOR ILLUMINATING BODY CAVITIES discloses a laryngoscope having a blade portion which is curved over substantially its entire length. The blade is mounted atop a handle having a light bulb mounted therein. The blade is fitted with a fiber optical light guide designed to convey light from the handle mounted light bulb to the working surface of the laryngoscope blade.

U.S. Pat. No. 4,432,350 entitled MEANS FOR APPLYING TOPICAL ANESTHESIA FOR USE WITH A LARYNGOSCOPE issued on Feb. 21, 1984 to Allan Breslaw and Bernard Broad is directed to a laryngoscope having a blade which is curved throughout its length. The blade is fitted with a device, adapted for applying a topical anesthesia as the blade is inserted into a patient's pharynx and larynx.

U.S. Pat. No. 4,314,551 issued Feb. 9, 1982 to Roger Kadell and entitled LARYNGOSCOPE discloses a curved laryngoscope blade which is movably mounted to a handle. The blade is manipulated by means of a lever handle mounted on the aft end of the blade.

U.S. Pat. No. 4,114,609 issued Sep. 19, 1977 to John Moses under the title LARYNGOSCOPE discloses a laryngoscope blade having an essential straight blade portion. An end portion of the blade, which is curved out of the plane of the straight blade portion, constitutes the inner end of the blade. In alternative embodiments (FIGS. 5 and 6), the straight blade portion of the blade is formed to be arcuate in cross-section.

U.S. Pat. No. 3,986,854 issued to Leonard Scrivo et al. on Oct. 17, 1976 under the title METHOD OF MAKING AUTOCLAVABLE INSTRUMENT WITH SINTERED FIBERGLASS ROD discloses a laryngoscope having a curved blade. The blade is fitted with an elongated glass rod including therein a plurality of glass fibers.

U.S. Pat. No. 3,826,248 issued on July 30, 1974 to Georg Gobels under the title LARYNGOSCOPE discloses a laryngoscope blade having a curved configuration. An insert of elastic material is mounted on the blade near the tongue deflector side of the blade.

U.S. Pat. No. 4,583,527 issued on Apr. 22, 1986 to Belmont Musicant et al. under the title DISPOSABLE CUSHIONING DEVICE FOR A LARYNGOSCOPE discloses a laryngoscope blade having a blade portion which is curved from its base to its tip. The blade appears to define a channel in the exterior surface thereof.

The periodical ANAESTHESIA, Vol. 39, Number 12, published December of 1984 includes an article entitled "Improved Vision Modification of the Macintosh Laryngoscope" by G. B. Racz. On pages 1249–1250 of that article a description of a laryngoscope blade having a blade portion which is curved throughout its length is disclosed. The blade portion defines a recessed channel defined within the exterior surface of the blade portion.

SUMMARY OF THE INVENTION

The instant invention is directed to an improvement in laryngoscope blades, and more particularly to a type of blade known generally in the art as a Macintosh blade. This type of blade is characterized by a blade portion which is curved throughout its entire length.

The blade portion of the invention includes a first end and a second end. The first end may be configured to form a base member adapted for mounting on a handle. In at least one embodiment this first end or base member is structured to define an angulated slot therein suited for mechanical cooperation with a handle.

The blade portion defines a recessed channel therein positioned approximately midway between the first end and the second end. This channel may have a substantially "U"-shaped configuration. When viewed in plan view, the channel may have a generally elliptical shape. The major axis of the ellipse is oriented substantially parallel to the longitudinal axis of the blade portion. The minor axis of the ellipse is oriented substantially perpendicular to that longitudinal axis. The channel has a width which varies dimensionally over the length of the channel. At the ends of the channel the width is at a minimum. The channel width reaches a maximum proximate a central region of the channel, i.e. approximately midway between the two opposing ends of the channel.

The channel depth also varies over the length of the channel. Proximate the central region of the channel the channel depth reaches a maximum. As one approaches either of the opposing ends of the channel from the direction of central region, the depth of the channel decreases until at the ends of the channel, the channel floor merges into the exterior surface of the blade portion.

A cylindrical, bar-like member is mounted transversely to the second end of the blade portion.

A wall member may be mounted to one side of the blade portion to extend uprightly therefrom in a direction opposite to that of the blade portion. The wall member defines an aperture therein in which may be mounted a lamp, e.g. a light bulb.

A shelf member may be mounted to the upright wall membrane to extend laterally from that wall membrane.

BRIEF DESCRIPTION OF THE DRAWINGS

FIG. 5 is a right side elevational view of the laryngoscope blade of FIG. 1 detailing the lamp placement within the upstanding wall member;

FIG. 6 is a left side elevational view of the laryngoscope blade of FIG. 1;

FIG. 7 is a top plan view of the laryngoscope blade of FIG. 1 detailing the elliptical recess channel within the blade portion.

DETAILED DESCRIPTION OF THE DRAWINGS

Figure 1:
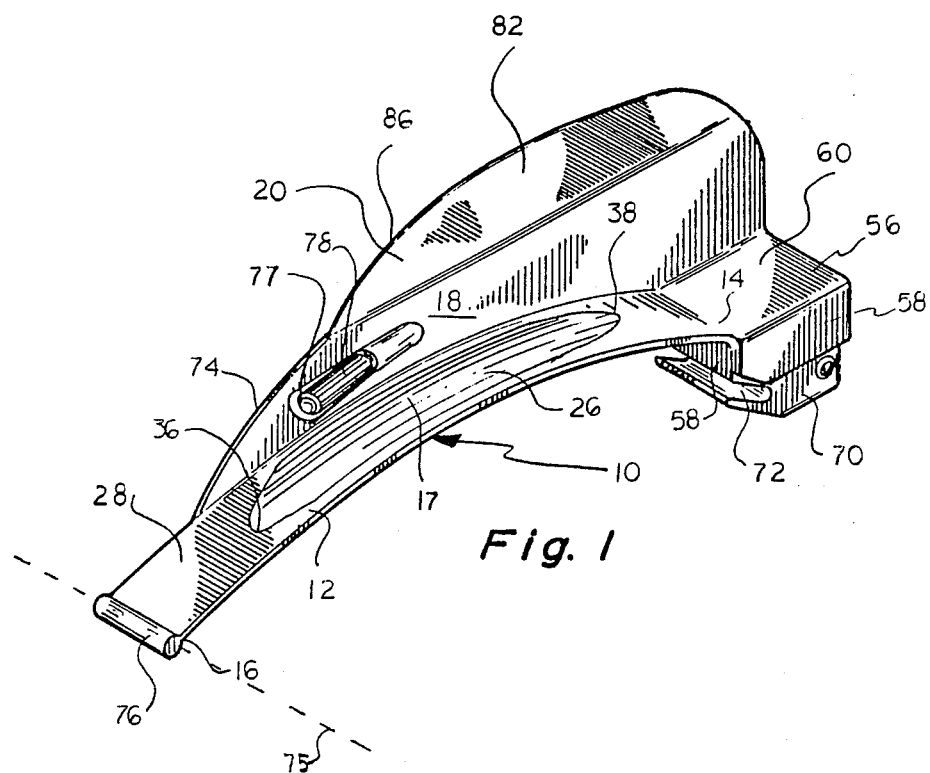
FIG. 1 is a perspective view of a laryngoscope blade embodying the improvement of the invention.

As shown to advantage in FIG. 1, a laryngoscope blade of the instant invention, generally 10 includes a blade portion 12, having two opposing ends 14 and 16, an upstanding wall member 18, mounted on that blade portion 12; and a laterally extending shelf 20 which is mounted to the wall member 18.

The blade portion 12 is fabricated from a relatively thin sheet of material to have a generally rectangular configuration when viewed in plan view, see FIG. 7. In plan view the blade portion defines two sides 22A and 22B which are oriented parallel to one another. The sides 22A and 22B are oriented parallel to the longitudinal axis 24 of the blade 10.

The ends 14 and 16 of the blade portion 12 are generally linear in configuration. The ends 14 and 16 are oriented substantially orthogonally to the sides 22A and 22B, thereby forming a member which appears to be rectangular-shaped in plan view.

The blade portion 12 is curved throughout its entire length, i.e. between ends 14 and 16. As shown in FIG. 6, the blade portion 12 defines a somewhat arcuate configuration when viewed from the side. It should be noted that the blade portion 12 as illustrated is not symmetric about a vertical axis 30. Instead, the blade portion 12 is curved along its entire length in a generally asymmetric fashion with reference to the axis 30.

The blade portion 12 defines a recessed channel 26 within its top exterior surface 28. As depicted in FIG. 7, the channel 26 has an elliptical shape when viewed in plan view. The channel 26 is oriented about a major axis 32 and a minor axis 34. The major axis 32 is positioned parallel to the longitudinal axis 24 of the blade 10. In referring to the axes of the channel 26 it should be understood that the channel 26 itself does not follow a straight linear path. As illustrated in FIGS. 1-3 and 5-6, the channel 26 follows a somewhat curved path, which, to a degree, approximates the curvature of the blade portion 12.

The channel 26 includes two opposing ends 36 and 38, a width 40 and a depth 42. The width 40 is defined as the distance between the curved sidewalls forming the channel 26 (shown in FIG. 3 as being measured laterally). In viewing the channel 26 as depicted in FIGS. 1-3 and 7, it is apparent that the width of the channel increases dimensionally as one proceeds from an end of the channel towards the channel's central region 41.

Figure 2:
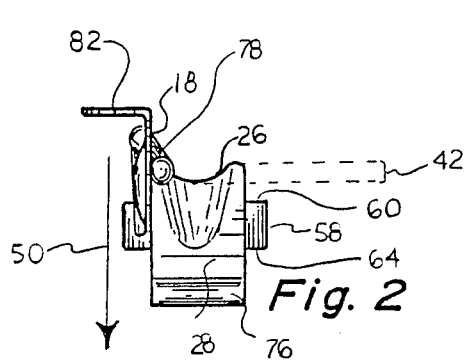
FIG. 2 is a front elevational view of the laryngoscope blade illustrated in FIG. 1.
Figure 3:
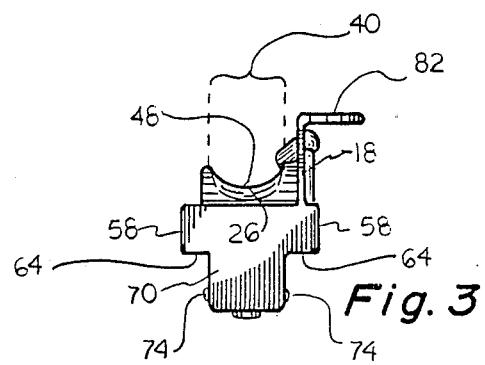
FIG. 3 is a rear elevated view of the laryngoscope blade of FIG. 1.

The channel 26 obtains a minimum width at each of its ends 36 and 38. A maximum width occurs in the central region of the channel 41. The width 40 of the channel 26 varies over the height, i.e. depth of the channel 26. As shown in FIGS. 2 and 3, the channel 26 is defined by a generally "U"-shaped sidewall. It follows therefore that the channel obtains its maximum width proximate the tip of the channel. The width decreases over the depth of the channel until reaching a minimum width at the member, bottom, or floor 48 of the channel.

As illustrated by FIGS. 1-3 and 5-6, the depth 42 of the channel also varies over the length of that channel. The depth is shown in the figures as being measured vertically in the direction of arrow 50, using the top surface 28 of the blade portion 12 as the reference point or benchmark. As shown in FIG. 1, the depth 42 of the channel reaches a minimum value dimensionally proximate each end 36 and 38. At each of those ends, the bottom, or floor 48 of the channel 26 actually merges into the top surface 28. The depth of the channel 26 increases dimensionally as one proceeds toward the central region 41 from an end (36 or 38) of the channel. The channel 26 obtains a maximum depth within the central region 41. The depth of the channel 26 and the dimensional variance of that channel over the length of the blade portion 12 is shown to advantage in FIGS. 5 and 6 wherein the lower surface 52 of the blade portion is shown reaching a maximum thickness proximate the location of the central region 41 of the channel 26.

As detailed in FIG. 7, the channel 26 is located within the blade portion 12 between its ends 14 and 16. Stated more specifically, the channel 26 is positioned approximately midway between the ends 14 and 16.

Figure 4:
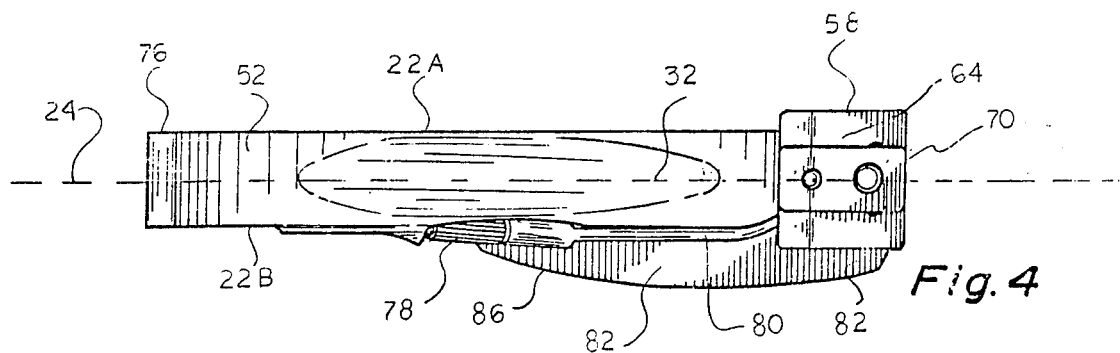
FIG. 4 is a bottom plan view of the laryngoscope blade of FIG. 1.

The end 14 of the blade portion 12 is mounted on a generally box-like base member 56. This base member 56 is illustrated as having upstanding planar sides 58 oriented to form a generally quadrilateral configuration (See FIG. 4). A planar top surface 60 is mounted atop the sides 58 to form a box-like construction. Similarly, a planar surface 64 is mounted on the sides 58 to form a bottom for the base 56.

An elongate member 70 is mounted on surface 64 to extend outwardly therefrom. Member 70 has a generally box-like outer configuration. Member 70 defines an angulated slot 72 therein which extends along a side of the member.

A pair of ball-like mountings 74 are mounted in opposing sides of member 70 to extend outwardly from that member.

Mounted on end 16 of blade portion 12 is an elongate, generally cylindrically shaped bar-like member 76. The longitudinal axis 75 of the bar-like member 76 is oriented generally transverse or orthogonal to the longitudinal axis 24 of the blade portion 12. The bar-like member 76 has a generally rounded surface along its length and two planar end sections.

A thin upright wall member 18 is mounted on side 22B of blade portion 12. As detailed in FIGS. 1 and 6, the wall member 18 extends in a direction opposite, i.e. orthogonal to the direction of the blade portion 12. The forward edge 74 of wall member 18 presents a curved configuration.

Wall member 18 defines an aperture 77 therein which is dimensioned to receive a lamp 78. The lamp 78 is connected to a conduit 80 which extends along the wall member 18 and is eventually mounted on base 56.

A shelf member 82, having a generally planar structure is orthogonally mounted atop wall member 72 to extend laterally therefrom. The shelf has a curved configuration 86 along its leading edge.

Those skilled in the art will recognize that the embodiment hereinbefore described is illustrative of the general principles of the invention. The embodiment herein described is not intended to limit the scope of the claims which themselves recite what applicants regard as their invention.

I claim:

1. A laryngoscope blade comprising:
a base member; and
a blade portion having a first end and an opposing second end, a top surface and a length, said first end being mounted on said base member; said blade portion being curved throughout said length thereof, said blade portion defining a recessed channel within said top surface, said channel having a generally elliptical shape and a length which is dimensionally less than said blade portion length.

2. The laryngoscope blade according to claim 1 wherein said blade portion is curved from said first end to said second end.

3. The laryngoscope blade according to claim 1 wherein an upright wall is mounted on said blade portion to extend in a direction opposite to said blade portion.

4. The laryngoscope blade according to claim 3 wherein a lateral shelf is mounted on said upright wall.

5. The laryngoscope blade according to claim 1 wherein a rounded bar-like member is mounted on said blade portion, contiguous said second end.

6. The laryngoscope blade according to claim 1 wherein said base member defines an angulated slot therein.

7. The laryngoscope blade according to claim 3 wherein said upright wall defines an aperture therein.

8. The laryngoscope blade according to claim 7 wherein a lamp is mounted within said aperture.

9. The laryngoscope blade according to claim 1 wherein said blade portion is arcuate in configuration.

10. The laryngoscope blade according to claim 1 wherein said channel is located approximately midway between said first end and said second end.

11. The laryngoscope blade according to claim 1 wherein said channel is substantially "U"-shaped in cross-section.

12. The laryngoscope blade according to claim 1 wherein said channel has a major axis oriented substantially parallel to a longitudinal axis of said blade portion.

13. The laryngoscope blade according to claim 1 wherein said channel has a first end, a second end, a central region and a depth, said channel having a maximum depth at said channel's central region and a minimum depth at said channel's first and second ends.

14. A laryngoscope blade comprising:
a base member defining a slot therein;
a blade portion having a first end and a second end, a top surface and a length, said first end being mounted on said base member, said blade portion being curved from said first end to said second end, thereby defining an arcuate-shaped configuration, said blade portion defining a generally "U"-shaped cross-section recessed channel within said top surface which extends along a portion of said blade portion length, said channel having a generally elliptical shape, said channel being located generally midway between said first end and said second end;
a rounded, bar-like member mounted on said second end;
an upright wall mounted on said blade portion extending in a direction opposite to said blade portion, said upright wall defining an aperture therein; and
a lamp mounted within said aperture.

15. The laryngoscope blade according to claim 14 wherein a lateral shelf is mounted on said upright wall.

16. The laryngoscope blade according to claim 14 wherein said elliptical shape of said channel has a major axis oriented substantially parallel to a longitudinal axis of said blade portion.

17. A laryngoscope blade comprising:
a base member defining an angulated slot therein;
a blade portion having a first end, a second end, a top surface and a length, said first end being mounted on said base member, said blade portion being arcuately curved over its entire length between said first end and said second end thereby defining an arcuate shape configuration, said blade portion defining a generally "U"-shaped cross-section recessed channel within said top surface which extends along a portion of said blade portion length, said channel having a generally elliptical shape, said channel having a major axis oriented substantially parallel to a longitudinal axis of said blade portion;
a rounded, bar-like member mounted on said second end;
an upright wall mounted on said blade portion extending in a direction opposite to said blade portion, said upright wall defining an aperture therein; and
a lamp mounted within said aperture.

* * * * *